(12) United States Patent
Conrad et al.

(10) Patent No.: US 7,237,554 B2
(45) Date of Patent: *Jul. 3, 2007

(54) AIRWAY IMPLANT

(75) Inventors: Timothy R. Conrad, Eden Prairie, MN (US); Susan L. Critzer, Dellwood, MN (US); Brian J. Erickson, Woodbury, MN (US); Anja K. Metzger, Stillwater, MN (US); John P. Sopp, Forest Lake, MN (US)

(73) Assignee: Restore Medical, Inc., St. Paul, MN (US)

( * ) Notice: Subject to any disclaimer, the term of this patent is extended or adjusted under 35 U.S.C. 154(b) by 586 days.

This patent is subject to a terminal disclaimer.

(21) Appl. No.: 10/698,819

(22) Filed: Oct. 31, 2003

(65) Prior Publication Data

US 2005/0092332 A1 May 5, 2005

(51) Int. Cl.
*A61F 5/56* (2006.01)
*A61B 19/00* (2006.01)
(52) U.S. Cl. .................. 128/897; 128/848; 128/898
(58) Field of Classification Search ............ 600/36–37; 128/848, 200.24, 897
See application file for complete search history.

(56) References Cited

U.S. PATENT DOCUMENTS

| | | | |
|---|---|---|---|
| 5,843,021 A | 12/1998 | Edwards et al. | |
| 5,979,456 A | 11/1999 | Magovern | |
| 5,988,171 A | 11/1999 | Sohn et al. | |
| 6,161,541 A | 12/2000 | Woodson | |
| 6,216,702 B1 | 4/2001 | Gjersøe | |
| 6,250,307 B1 | 6/2001 | Conrad et al. | |
| 6,408,851 B1 | 6/2002 | Karell | |
| 6,431,174 B1 | 8/2002 | Knudson et al. | |
| 6,523,542 B2 | 2/2003 | Metzger et al. | |
| 6,601,584 B2 | 8/2003 | Knudson et al. | |
| 6,748,950 B2 | 6/2004 | Clark et al. | |
| 2001/0050084 A1 | 12/2001 | Knudson et al. | |

(Continued)

FOREIGN PATENT DOCUMENTS

DE 44 12 190 A1 10/1995

(Continued)

OTHER PUBLICATIONS

Ersek et al., "Minimally Invasive Macro Implants," *Worldplast*, vol. I, No. 4, pp. 275-285 (1996).

(Continued)

*Primary Examiner*—Charles A. Marmor, II
*Assistant Examiner*—Christine Hopkins
(74) *Attorney, Agent, or Firm*—Merchant & Gould P.C.

(57) ABSTRACT

A method and apparatus are disclosed for treating a condition of a patient's airway. The condition is attributed at least in part to a spacing of tissue from opposing surfaces in the airway. In one embodiment, the method and apparatus include placing a tissue contractor within the tissue. The contractor includes a static end and a tissue in-growth engaging end. The static end is secured to a bony structure adjacent to tissue to be contracted. The tissue in-growth engaging end is secured to the tissue and spaced from the bony structure. A spacing between the tissue engaging end and a bony end is contracted in order to place the tissue under tension.

14 Claims, 5 Drawing Sheets

U.S. PATENT DOCUMENTS

| | | |
|---|---|---|
| 2001/0050085 A1 | 12/2001 | Knudson et al. |
| 2002/0035994 A1* | 3/2002 | Stevens et al. ............. 128/848 |
| 2002/0049479 A1 | 4/2002 | Pitts |
| 2004/0045556 A1 | 3/2004 | Nelson et al. |
| 2004/0073272 A1* | 4/2004 | Knudson et al. ............. 607/48 |
| 2004/0134491 A1 | 7/2004 | Pflueger et al. |
| 2004/0139975 A1 | 7/2004 | Nelson et al. |
| 2004/0149290 A1 | 8/2004 | Nelson et al. |
| 2004/0153127 A1 | 8/2004 | Gordon et al. |

FOREIGN PATENT DOCUMENTS

| | | |
|---|---|---|
| DE | 199 20 114 A1 | 11/2000 |
| EP | 1039859 B1 | 12/1998 |
| WO | WO/2004/021869 A2 | 3/2004 |
| WO | WO/2004/021870 A2 | 3/2004 |
| WO | WO 2005/044158 A1 | 5/2005 |
| WO | WO 2005/082452 A1 | 9/2005 |
| WO | WO 2006/072571 A1 | 7/2006 |

OTHER PUBLICATIONS

Thomas, A. et al., "Preliminary findings from a prospective, randomized trial of two tongue-base surgeries for sleep-disordered breathing," *Otolaryngology-Head and Neck Surgery*, vol. 129, No. 5, pp. 539-546 (Nov. 2003).

Eisle et al., "Direct Hypoglossal Nerve Stimulation in Obstructive Sleep Apnea", *Arch. Otolaryngol. Head Neck Surg.*, vol. 123, pp. 57-61 (1997).

Miller et al., "Role of the Tongue Base Suspension Suture with the Repose System Bone Screw in the Multilevel Surgical Management of Obstructive Sleep Apnea", *Otolaryngol. Head Neck Surg.*, vol. 126, pp. 392-398 (2002).

Powell et al., "Radiofrequency Tongue Base Reduction in Sleep-Disordered Breathing: A pilot study", *Otolaryngol. Head Neck Surg.*, vol. 120, pp. 656-664 (1999).

Powell et al., "Radiofrequency Volumetric Reduction of the Tongue—A Porcine Pilot Study for the Treatment of Obstructive Sleep Apnea Syndrome", *Chest*, vol. 111, pp. 1348-1355 (1997).

\* cited by examiner

AIRWAY IMPLANT

I. BACKGROUND OF THE INVENTION

1. Field of the Invention

This invention pertains to a method and apparatus for treating a condition of an upper airway of a patient. More particularly, this invention is directed to such a method and apparatus including an implant to improve patency of the airway.

2. Description of the Prior Art

Upper airway conditions such as obstructive sleep apnea ("OSA") and snoring have received a great deal of attention. These conditions have recognized sociological and health implications for both the patient and the patient's bed partner.

Numerous attempts have been made towards treating OSA and snoring. These include placing implants in either the tissue of the soft palate or the pharyngeal airway as disclosed in commonly assigned U.S. Pat. No. 6,250,307 to Conrad et al. dated Jun. 26, 2003, U.S. Pat. No. 6,523,542 to Metzger et al. dated Feb. 25, 2003 and U.S. Pat. No. 6,431,174 to Knudson et al. dated Aug. 13, 2002. Further, U.S. Pat. No. 6,601,584 to Knudson et al. dated Aug. 5, 2003 teaches a contracting implant for placement in the soft palate of the patient.

In the '584 patent, an embodiment of the contracting implant includes two tissue attachment ends (for example ends 102b in FIGS. 46 and 47) which are maintained in a space-apart, stretched relation by a bio-resorbable member 102c which surrounds an internal spring or resilient member 102a. After implantation, tissue grows into the attachment ends 102b. The bioresorbable member 102c is selected to resorb after the tissue in-growth permitting the resilient member 102a to contract drawing ends 102b together as illustrated in FIG. 47 of the '584 patent (incorporated herein by reference). Tissue contraction is believed to be desirable in that the tissue contraction results in a debulking of the tissue and movement of tissue away from opposing tissue surfaces in the pharyngeal upper airway.

Another prior art technique for treating OSA or snoring is disclosed in U.S. Pat. No. 5,988,171 to Sohn et al. dated Nov. 23, 1999. In the '171 patent, a cord (e.g., a suture material) (element 32 in FIG. 6 of the '171 patent) is placed surrounding a base of the tongue and secured to the jaw by reason at an attachment member (element 20 in FIG. 6 of the '171 patent). In the method of the '171 patent, the member 32 can be shortened to draw the base of the tongue toward the jaw and thereby move the tissue of the base of the tongue away from the opposing tissue of the pharyngeal airway. However, this procedure is often uncomfortable. This procedure, referred to as tongue suspension, is also described in Miller et al., "Role of the tongue base suspension suture with The Repose System bone screw in the multilevel surgical management of obstructive sleep apnea", *Otolaryngol. Head Neck Surg.*, Vol. 126, pp. 392-398 (2002).

Another technique for debulking tissue includes applying radio frequency ablation to either the tongue base or of the soft palate to debulk the tissue of the tongue or palate, respectively. This technique is illustrated in U.S. Pat. No. 5,843,021 to Edwards et al. dated Dec. 1, 1998. RF tongue base reduction procedures are described in Powell et al., "Radiofrequency tongue base reduction in sleep-disordered breathing: A pilot study", *Otolaryngol. Head Neck Surg.*, Vol. 120, pp. 656-664 (1999) and Powell et al., "Radiofrequency Volumetric Reduction of the Tongue—A Porcine Pilot Study for the Treatment of Obstructive Sleep Apnea Syndrome", *Chest*, Vol. 111, pp. 1348-1355 (1997).

A surgical hyoid expansion to treat OSA is disclosed in U.S. Pat. No. 6,161,541 to Woodson dated Dec. 19, 2000. Other tongue treatments for OSA include stimulation of the hypoglossal nerve. This procedure is described in Eisle et al., "Direct Hypoglossal Nerve Stimulation in Obstructive Sleep Apnea", *Arch. Otolaryngol. Head Neck Surg.*, Vol. 123, pp. 57-61 (1997).

II. SUMMARY OF THE INVENTION

According to a preferred embodiment to the present invention a method and apparatus are disclosed for treating a condition of a patient's airway. The condition is attributed at least in part to a spacing of tissue from opposing surfaces in the airway. In one embodiment, the method and apparatus include placing a tissue contractor within the tissue. The contractor includes a static end and a tissue in-growth engaging end. The static end is secured to a bony structure adjacent to tissue to be contracted. The tissue in-growth engaging end is secured to the tissue and spaced from the bony structure. A spacing between the tissue engaging end and a bony end is contracted in order to increase the airway geometry.

III. BRIEF DESCRIPTION OF THE DRAWINGS

IV. DESCRIPTION OF THE PREFERRED EMBODIMENT

With reference now to the various drawing figures in which identical elements are numbered identically throughout, a description of the preferred embodiment of the present invention will now be provided. To facilitate a description and an understanding of the present invention, the aforementioned U.S. Pat. Nos. 6,250,307; 6,523,542; 6,431,174; 6,601,584; 5,988,171 and 5,843,021 are hereby incorporated herein by reference.

Figure 1:
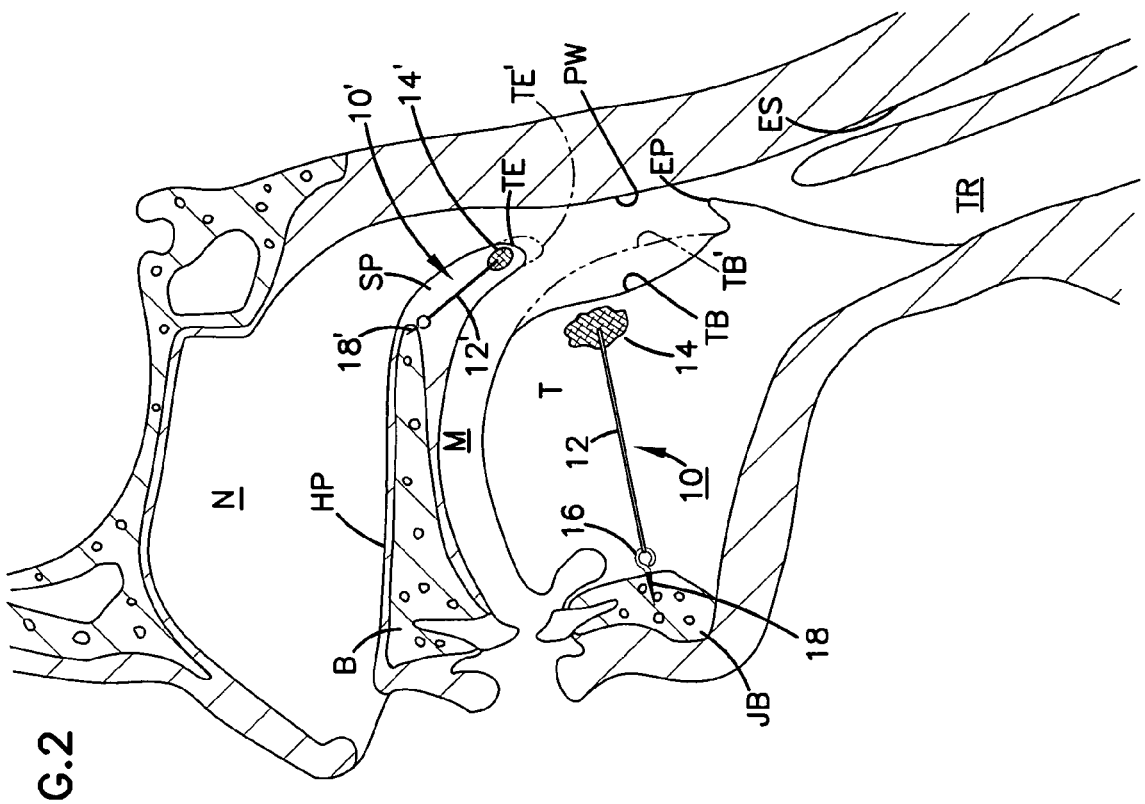
FIG. 1 is a side elevation, schematic view of a patient illustrating structure defining an upper airway of the patient and showing an implant according to an embodiment of the present invention positioned within the soft palate and secured to the bony structure of a hard palate and showing a similar implant in the tongue and secured to the bony structure of the jaw.

With initial reference to FIG. 1, a soft palate SP is shown in side elevation view extending from a bony portion of a hard palate HP. The soft palate SP extends rearward to a trailing end TE. FIG. 1 also illustrates a tongue T with a base TB opposing a pharyngeal wall PW. A jawbone JB is shown at the lower front of the tongue T.

As a first described embodiment of the present invention, an implant 10 is shown in FIG. 1 completely implanted within the tongue T. A similar implant 10' is fully implanted in the soft palate SP. As will be apparent, implants 10, 10' are functionally and structurally similar differing only in size to facilitate placement in the tongue T and soft palate SP, respectively. As a result, a description of implant 10 will suffice as a description of implant 10' (with similar elements similarly numbered with the addition of an apostrophe to distinguish the implants 10, 10'). Further, while both implants 10, 10' are shown implanted in the same patient, either could be separately implanted.

The implant 10 includes an elongated member 12 having a tissue in-growth end 14 and a static end 16. The tissue in-growth end 14 may be any tissue growth inducing material (e.g., felt or PET) to induce growth of tissue into the end 14 to secure the end 14 to surrounding tissue following implantation. The elongated member 12 may be suture material one end secured to the felt 14 and with the static end 16 being a free end of the suture material 12.

An anchor 18 (in the form of a treaded eye-bolt) is secured to the jawbone JB. In the case of implant 10', the anchor 18' is secured to the bone of the hard palate. The end 16 is secured to the anchor 18.

The end 14 is placed in the tongue near the tongue base TB. A surgeon adjusts a tension of the suture 12. This causes the tongue base TB to be urged toward the jawbone JB thereby placing the tissue of the tongue in compression. When a desired tension is attained, the surgeon may tie off the static end 16 at the bolt 18 retaining the tissue of the tongue T under tension. This method and apparatus provides a resistance to movement of the tongue base TB toward the pharyngeal wall PW. Similarly, with implant 10', the trailing end TE of the soft palate SP is urged away from the back of the throat and the soft palate SP is prevented from lengthening.

Figure 2:
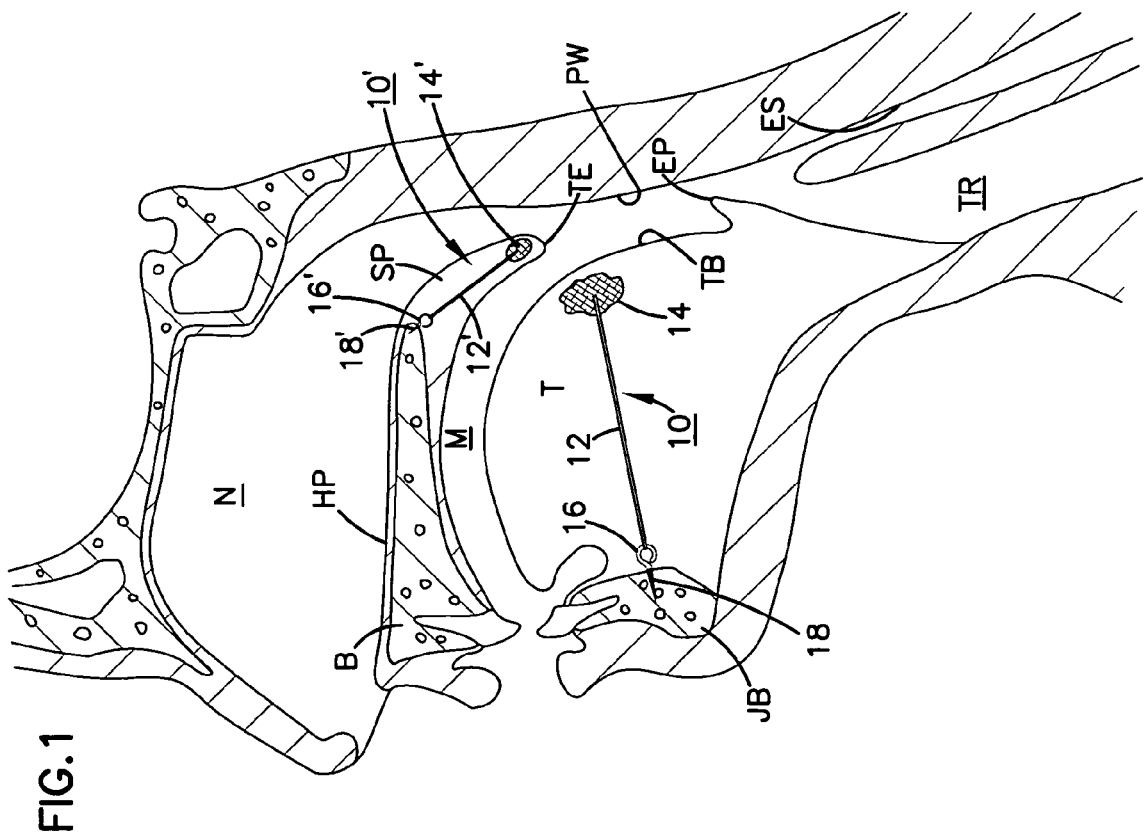
FIG. 2 is the view of FIG. 1 following contracting of the implants in the palate and tongue.

Placing the implants 10, 10' under tension as in FIG. 1 provides therapy in that the tongue base TB and soft palate trailing end TE are retained from movement toward the pharyngeal wall PW. In addition, at time of initial implantation or thereafter, a surgeon may obtain access to anchors 18, 18' and further shorten the length of the elongated member 12 (i.e., by pulling the member 12 through the bolt 18, 18') to draw the tongue base or trailing end away from the pharyngeal wall to a new profile. This is illustrated in FIG. 2 with the contracted profile shown in solid lines TB, TE and contrasted with the original profile shown in phantom lines TB', TE'.

Figure 3:
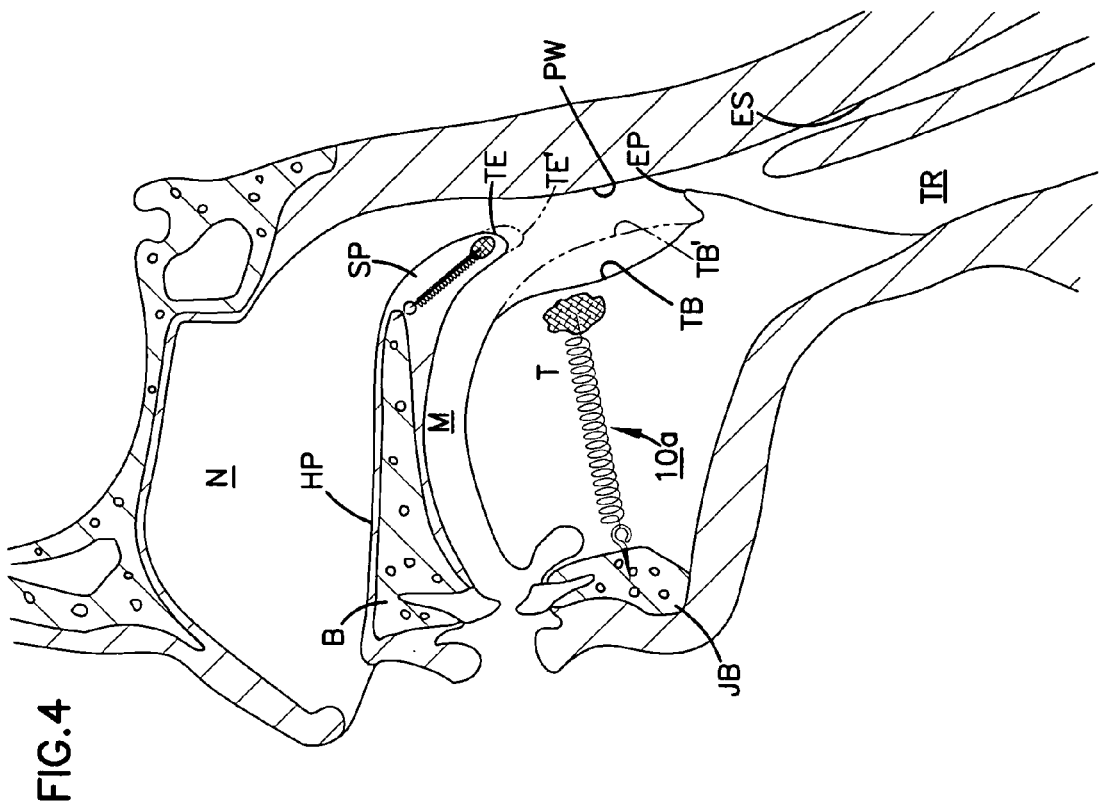
FIG. 3 is a view similar to that of FIG. 1 and showing an alternative embodiment of the present invention with implants of the alternative embodiment implanted in both the soft palate and tongue.
Figure 4:
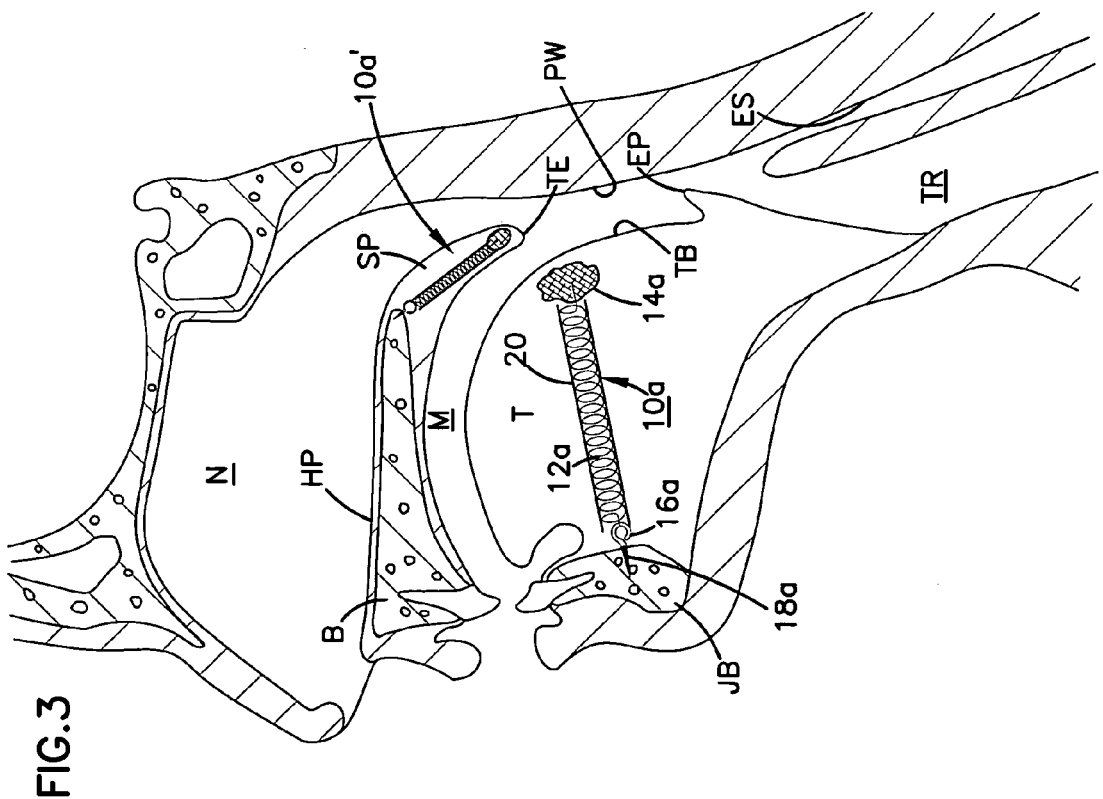
FIG. 4 is the view of FIG. 3 showing the implants in a contracted state.

Referring to FIGS. 3 and 4, an alternative embodiment of the present invention is shown as a implant 10a for the tongue T or implant 10a' for the soft palate SP. As with the embodiments of FIGS. 1 and 2, implants 10a, 10a' are functionally and structurally similar differing only in size to facilitate placement in the tongue and soft palate, respectively. As a result, a description of implant 10a will suffice as a description of implant 10a' (with similar elements similarly numbered with the addition of an apostrophe to distinguish the implants 10a, 10a'). Further, both implants 10a, 10a' are shown implanted in the same patient. Either or both implants could be implanted.

Implant 10a includes a tissue engaging end 14a and static end 16a. As in the embodiment of FIG. 1, the static end 16a is secured to a hard palate at the eyelet of an eyebolt 18a secured to the jawbone JB. Again, as in the embodiment of FIG. 1, the tissue-engaging end 14a may be any material which encourages tissue in-growth and attachment to tissue. An example of such a material may be PET or a felt material.

The tissue engaging end 14a and the static end 16a are connected by a resilient elongated member 12a which may be in the form of a spring member such as nitinol or other member which may be stretched to create a bias urging ends 14a, 16a toward one another. Opposing the bias of the spring member 12a is a bioresorbable material 20 positioned between the tissue-engaging end 14a and the bolt 18a.

After placement of the implant 10a within the tissue of the tongue and with the end 14a near the tongue base TB, the bio-resorbable material 20 will later resorb into the tissue of the tongue T permitting end 14a to be urged toward bolt 18a by the resilience of the spring 12a. This is illustrated in FIG. 4, where the contracted implant 10a places the tissue of the tongue under tension and urging the tongue base TB away from the pharyngeal wall PW. In FIG. 4, the contracted profile of the tongue base TB (and soft palate trailing end TE) is shown in solid lines and the original profile TB' (TE') is shown in phantom lines.

Figure 5:
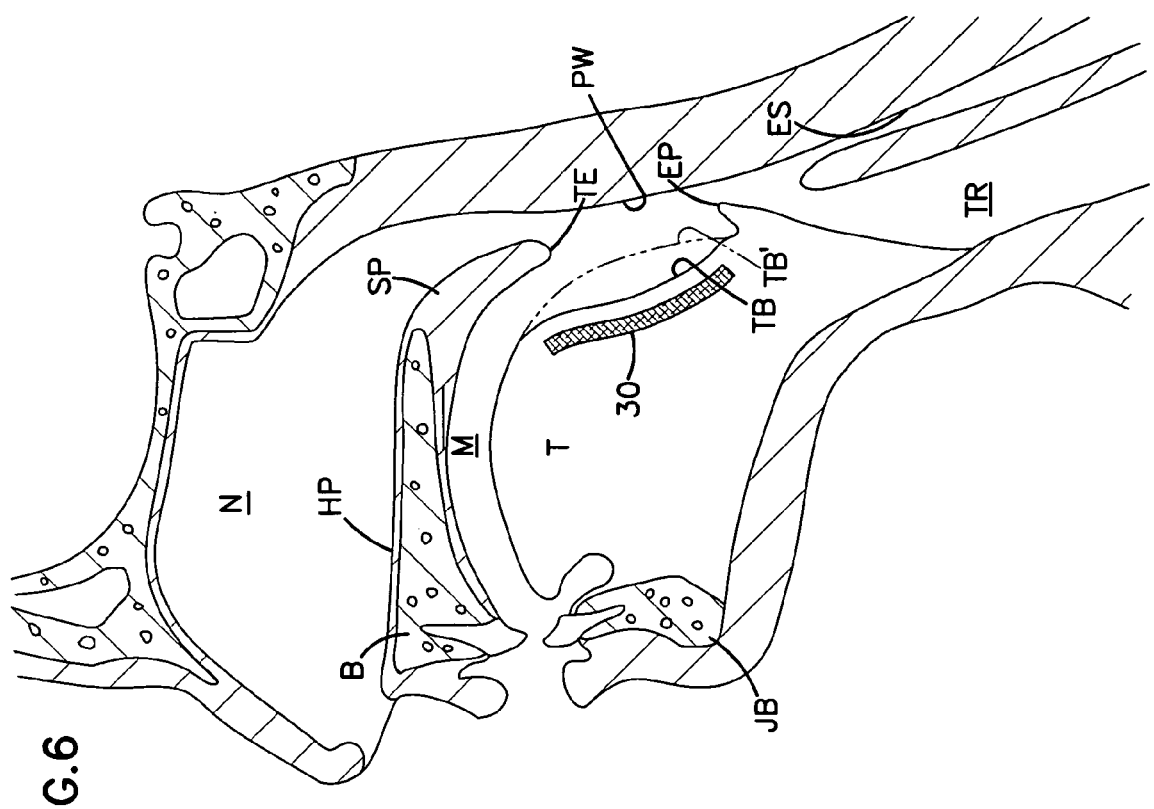
FIG. 5 is a view similar to that of FIG. 1 and showing a further alternative embodiment of the present invention with an implant of the further alternative embodiment implanted in the tongue.
Figure 6:
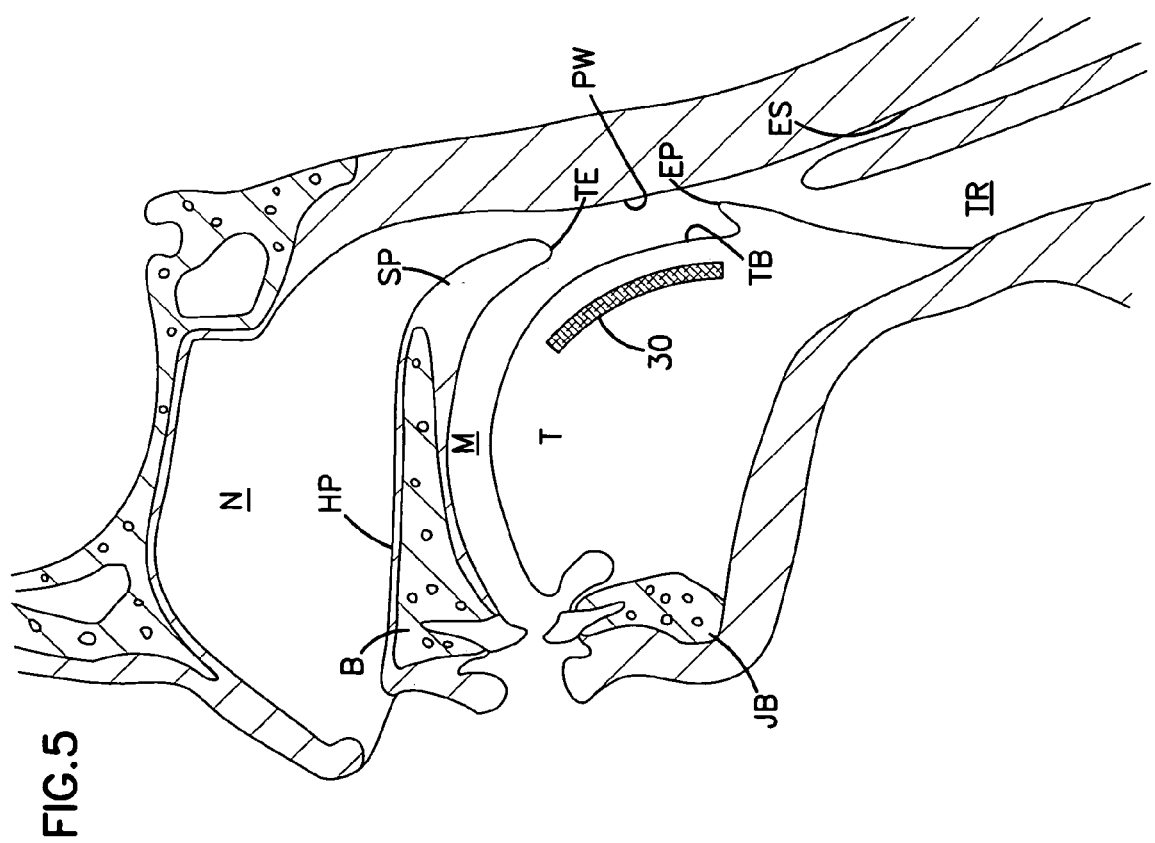
FIG. 6 is the view of FIG. 5 contraction of tissue around the implant.
Figure 7:
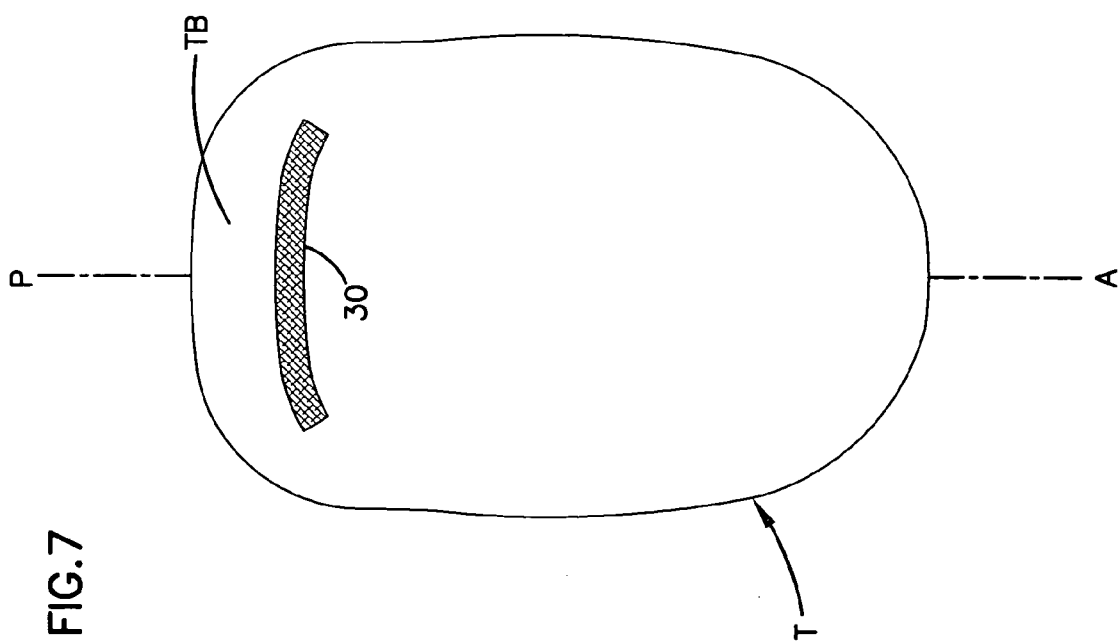
FIG. 7 is a top plan view of FIG. 5 showing an anterior-posterior axis A-P of the tongue.

FIGS. 5-7 illustrate a still further embodiment for reducing the tongue base TB. In this embodiment, a sheet 30 of tissue in-growth material (e.g., a sheet of felt with numerous interstitial space) is place in the tongue near the base TB. The sheet 30 is placed beneath the tongue surface and parallel to the base TB substantially covering the area of the tongue base TB. Scarring from the material contracts over time resulting in a reduction in the tongue base as illustrated in FIG. 6. To heighten the amount of tongue base reduction, the sheet 30 may be impregnated with a tissue reducing agent (e.g., a sclerosing agent).

Figure 10:
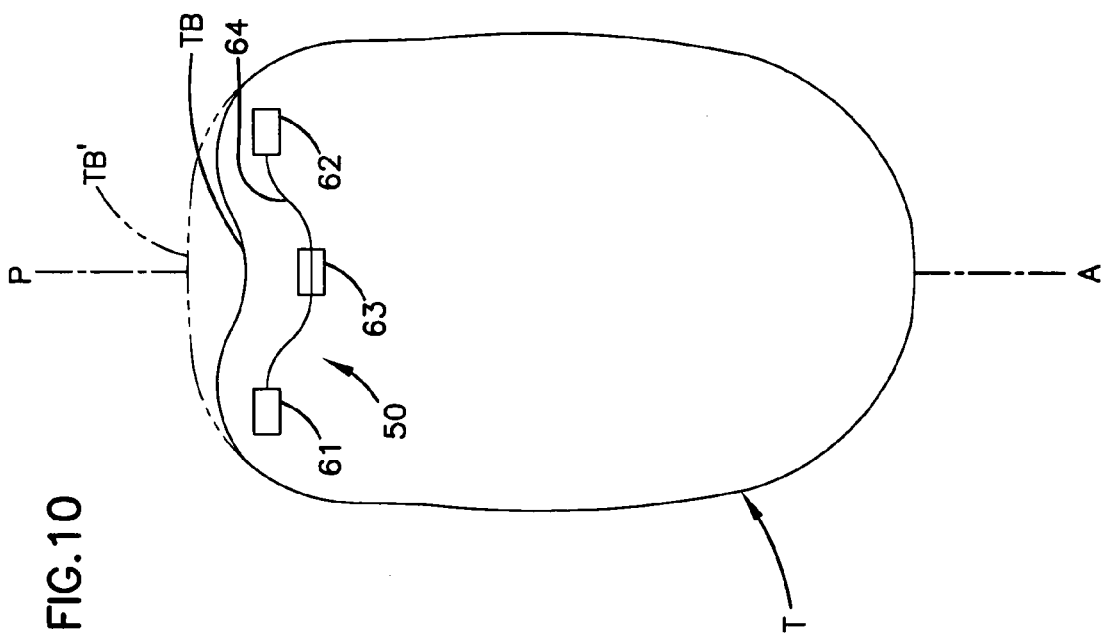
FIG. 10 is the view of FIG. 9 following tissue in-growth and resorption of bio-resorbable elements.
Figure 9:
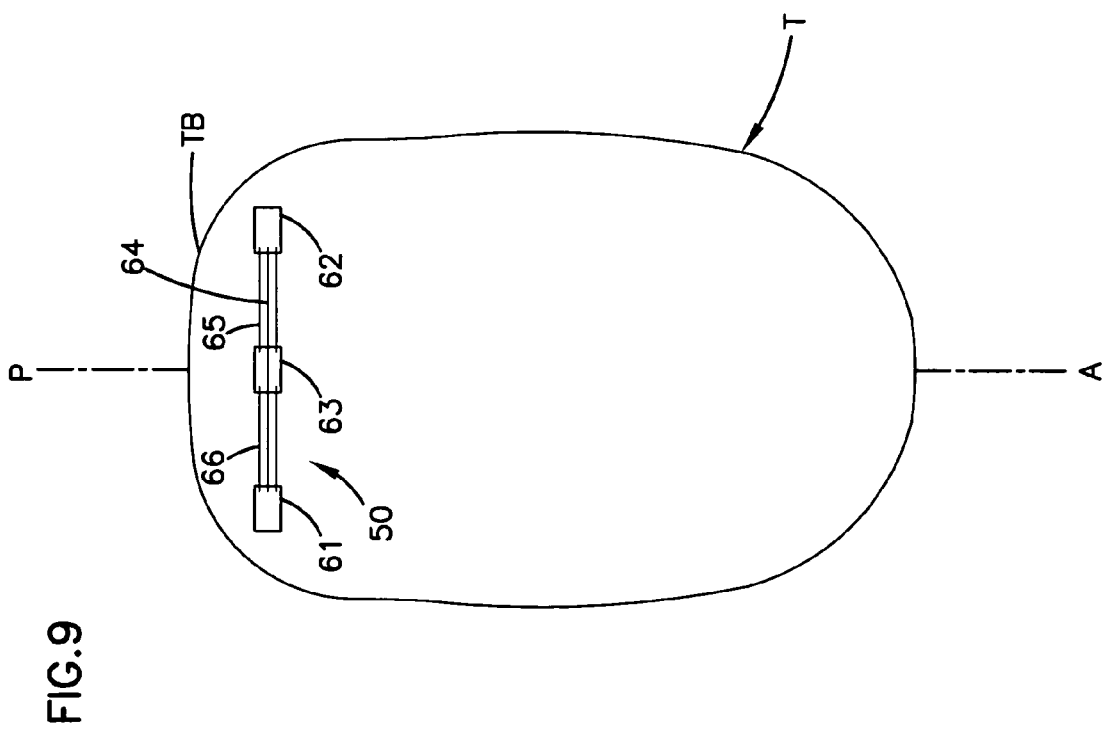
FIG. 9 is a view similar to FIG. 7 showing immediate post-implant of a still further embodiment of the present invention.

FIGS. 9 and 10 illustrate a further variant of FIGS. 5-7. The implant 50 includes three tissue in-growth pads 61, 62, 63. A nitinol bar 64 connects the pads 61-63 in-line with pad 63 centrally positioned. The bar 64 is pre-stressed to have a central bend shown in FIG. 10. Bio-resorbable sleeves 65, 66 hold the bar 64 in a straight line against the bias of bar 64 as in FIG. 9. The implant 50 is implanted as shown in FIG. 9 with the straight bar 64 parallel to the tongue base TB. After implantation, tissue grows into pads 61-63. After the time period of in-growth, the sleeves resorb as in FIG. 10. With the sleeves resorbed, the bar 64 bends to its pre-stressed shape. The tongue base moves with the pad 63 to reposition the tongue base (illustrated in FIG. 10 as the shift from TB' to TB).

Figure 8:
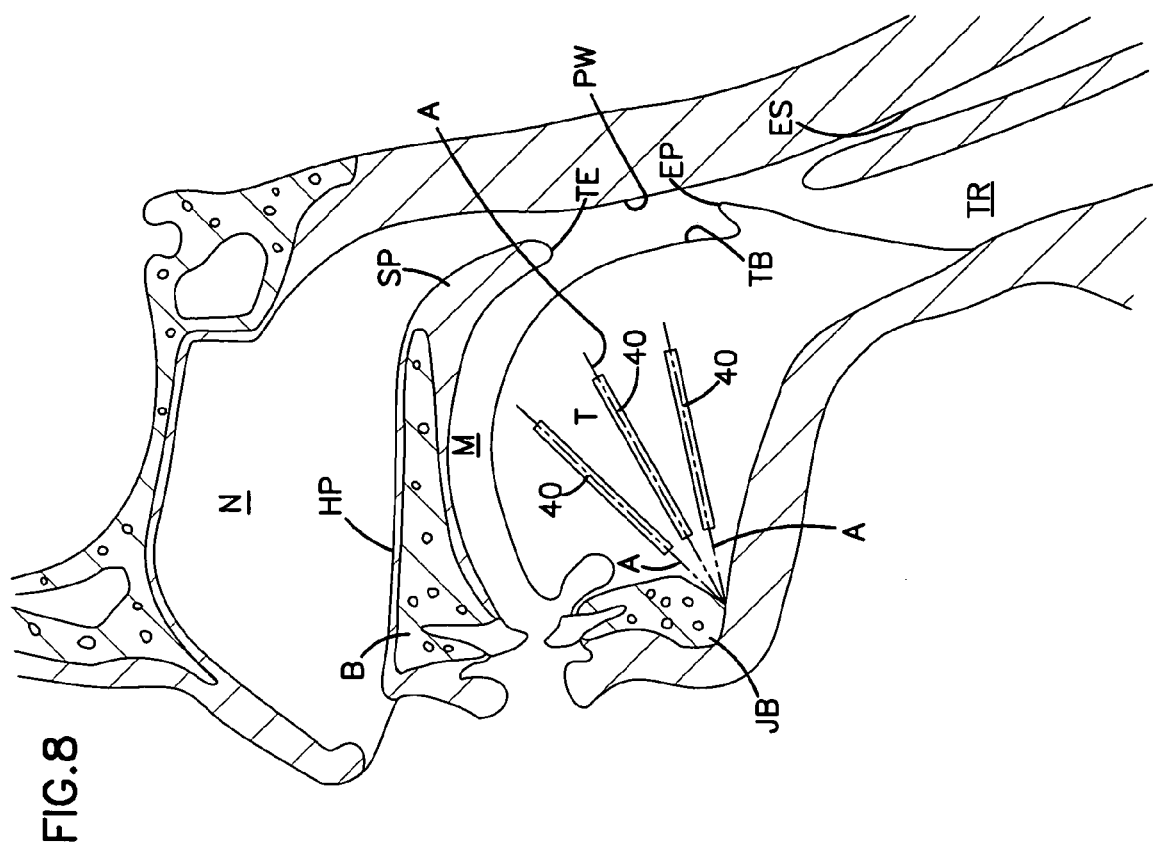
FIG. 8 is a view similar to that of FIG. 1 and showing a yet further alternative embodiment of the present invention with an implants of the yet further alternative embodiment implanted in the tongue.

FIG. 8 illustrates a still further embodiment of the invention for reducing the tongue base. Certain muscles of the tongue (particularly, the genioglossus muscles) radiate from the jawbone JB to the tongue surface as illustrated by lines A in FIG. 8. Contacting implants 40 identical to those in FIGS. 46 and 47 of U.S. Pat. No. 6,601,584 are placed with a contracting axis (the axis between tissue in-growth ends 14a'—identical to ends 102b in FIGS. 46, 47 of the '584 patent) are placed in the tongue in-line with the muscle radiating lines A. Alternatively, the contracting implant 40 may be of the construction shown in FIGS. 48 and 49 of the '584 patent. As the implants contract over time, they urge the tongue from collapsing toward the pharyngeal wall. In lieu of contracting implants, the elongated implants can be static implants such as implants shown in FIG. 11 of U.S. Pat. No. 6,250,307 and labeled 20.

The foregoing describes numerous embodiments of an invention for an implant for the tongue and soft palate to restrict tissue movement toward the pharyngeal wall. Having described the invention, alternatives and embodiments may occur to one of skill in the art. It is intended that such modifications and equivalents shall be included within the scope of the following claims.

What is claimed is:

1. A method for treating a condition of a patient's airway wherein the condition is attributed at least in part to a spacing of a base of a tongue from opposing pharyngeal wall surfaces in the airway; the method comprising:
    placing a tissue contractor within the tongue of the patient, the contractor including a tissue-engaging end connected to a member;
    the tissue-engaging end formed of a tissue growth inducing material to induce tissue in-growth into the tissue-engaging end following implantation in the tongue;
    the placing including placing the tissue-engaging end within an interior of said tongue near the base of the tongue and with the member extending from the tissue engaging end to an end near a jaw bone of the patient;
    anchoring the end of the member to the jaw bone for the member to resist movement of the tissue-engaging member away from the jaw bone; and
    wherein the anchoring is performed after at least partially securing the tissue-engaging end to the tissue.

2. A method according to claim 1 wherein said anchoring includes pulling on the contractor near the jaw bone and securing the contractor to the jaw bone with the tongue under tension.

3. A method according to claim 1 wherein the condition is snoring.

4. A method according to claim 1 wherein the condition is sleep apnea.

5. A method according to claim 1 wherein the member is secured directly to the jaw bone.

6. A method according to claim 1 wherein the member is a suture material.

7. A method according to claim 1 wherein the anchoring performed after an initial implantation of the tissue contractor by accessing the member and drawing on the member to draw the tissue-engaging end toward the jaw bone and then anchoring the end of the member to the jaw bone.

8. A method according to claim 1 wherein the member is a resilient material.

9. An apparatus for treating a condition of a patient's airway wherein the condition is attributed at least in part by a spacing of a base of a tongue from opposing pharyngeal wall surfaces; the apparatus comprising:
    a tissue contractor dimensioned so as to be placed within the tongue, the contractor including a tissue-engaging end connected to a member;
    an anchor for securing the member in place near a jaw bone;
    the tissue-engaging end formed of a tissue growth inducing material to induce tissue in-growth into the tissue-engaging end following implantation in the tongue;
    the member adapted to be accessed and secured by the anchor to the jaw bone following initial implantation of the tissue contractor.

10. An apparatus according to claim 9 wherein the condition is snoring.

11. An apparatus according to claim 9 wherein the condition is sleep apnea.

12. An apparatus according to claim 9 wherein the member is adapted to be secured directly to the bony structure.

13. An apparatus according to claim 9 wherein the member is a suture material.

14. An apparatus according to claim 9 wherein the member is a resilient material.

* * * * *